US009551737B2

(12) United States Patent
Bloemendaal et al.

(10) Patent No.: US 9,551,737 B2
(45) Date of Patent: *Jan. 24, 2017

(54) GRAIN BIN CAPACITIVE MOISTURE SENSOR SYSTEM AND METHOD

(75) Inventors: Brent J. Bloemendaal, Zionsville, IN (US); Raymond George Benson, Jr., Coatesville, IN (US)

(73) Assignee: CTB, Inc., Milford, IN (US)

( * ) Notice: Subject to any disclaimer, the term of this patent is extended or adjusted under 35 U.S.C. 154(b) by 556 days.

This patent is subject to a terminal disclaimer.

(21) Appl. No.: 13/569,804

(22) Filed: Aug. 8, 2012

(65) Prior Publication Data

US 2014/0043048 A1 Feb. 13, 2014

(51) Int. Cl.
*G01R 27/26* (2006.01)
*G01N 27/22* (2006.01)

(52) U.S. Cl.
CPC ......... *G01R 27/2605* (2013.01); *G01N 27/223* (2013.01)

(58) Field of Classification Search
CPC .... G01R 27/2605; G01R 27/26; G01N 27/223
USPC .......................................... 324/658–600, 694
See application file for complete search history.

(56) References Cited

U.S. PATENT DOCUMENTS

| | | | | |
|---|---|---|---|---|
| 3,509,456 A | * | 4/1970 | Zurbrick | G01R 27/26 324/686 |
| 3,707,249 A | * | 12/1972 | Tomlinson | B65G 65/00 222/564 |
| 3,959,723 A | * | 5/1976 | Wagner | G01R 27/2605 324/668 |
| 4,037,527 A | | 7/1977 | Steffen | |
| 4,145,176 A | | 3/1979 | Nelson | |

(Continued)

FOREIGN PATENT DOCUMENTS

| | | |
|---|---|---|
| EP | 2535902 A1 | 12/2012 |
| UA | 6252 U | 4/2005 |
| WO | WO2011033539 | 3/2011 |

OTHER PUBLICATIONS

Shinghal et al., "Intelligent Humidity Sensor for-Wireless Sensor Network Agricultural Application Application", International Journal of Wireless & Mobile Networks (IJWMN), vol. 3, No. 1, Feb. 2011, p. 118-128.*

(Continued)

*Primary Examiner* — Jermele M Hollington
*Assistant Examiner* — Douglas X Rodriguez
(74) *Attorney, Agent, or Firm* — Harness, Dickey

(57) ABSTRACT

A data collector associated with a grain bin is in communication with a plurality of capacitive moisture cables hanging within the grain bin. Each capacitive moisture cable includes a plurality of sensor nodes positioned along the moisture cable. Each sensor node includes a sensor node microprocessor and a sensor node memory coupled to a temperature sensor, a reference capacitive sensor and a capacitive moisture sensor. A main controller is in communication with the data collector. The main controller memory is configured in a data structure comprising grain type data, temperature data, raw reference capacitance data, raw moisture capacitance data, node identification data, physical node positional data, and a calculated moisture content for each sensor node. A method of determining moisture contents of grain in a grain bin related to such a system is also included.

32 Claims, 10 Drawing Sheets

(56) References Cited

U.S. PATENT DOCUMENTS

| | | | |
|---|---|---|---|
| 4,281,489 A | 8/1981 | Kallestad et al. | |
| 4,306,490 A | 12/1981 | Kallestad | |
| 4,522,335 A | 6/1985 | Kallestad et al. | |
| 4,583,300 A * | 4/1986 | Mast | 34/557 |
| 4,599,809 A * | 7/1986 | Parkes | 34/484 |
| 4,688,332 A | 8/1987 | Kallestad et al. | |
| 4,896,795 A * | 1/1990 | Ediger et al. | 222/63 |
| 4,930,229 A | 6/1990 | Moser | |
| 5,716,272 A * | 2/1998 | Nelson | 460/7 |
| 5,893,218 A | 4/1999 | Hunter et al. | |
| 5,937,023 A * | 8/1999 | Wu | G01D 5/24 377/12 |
| 6,530,160 B1 | 3/2003 | Gookins | |
| 7,004,401 B2 | 2/2006 | Kallestad | |
| 7,240,029 B2 | 7/2007 | Kallestad | |
| 7,243,857 B2 | 7/2007 | Kallestad | |
| 7,472,070 B2 | 12/2008 | Kallestad | |
| 8,677,845 B2 * | 3/2014 | Pacheco Da Cunha | G01N 33/10 73/866 |
| 8,806,772 B1 * | 8/2014 | Schaefer, Jr. | 34/89 |
| 2003/0079365 A1 | 5/2003 | Corak et al. | |
| 2003/0214310 A1 * | 11/2003 | McIntosh | G01N 27/223 324/658 |
| 2006/0100745 A1 | 5/2006 | Kallestad | |
| 2006/0108434 A1 | 5/2006 | Kallestad | |
| 2009/0211110 A1 | 8/2009 | Bartol | |
| 2011/0174072 A1 * | 7/2011 | Pacheco Da Cunha | G01N 33/10 73/431 |

OTHER PUBLICATIONS

Kadala et al., "Nondestructive Measurement of Moisture Content Using a Parallel-Plate Capacitance Sensor for Grain and Nuts", IEEE Sensors Journal, vol. 10, No. 7, Jul. 2010, pp. 1282-1287.*
McIntosh et al., "Fringing Field Capacitance Sensor for Measuring the Moisture Content of Agricultural Commodities", IEEE Sensors Journal, vol. 8, No. 3, Mar. 2008, p. 240-247.*
Skulski et al., "Planar Resonator Sensor for Moisture Measurements", 12th International Conference on Microwave and Radar, 1998, p. 692-695.*
Markov, "System for Maintenance of Optimal Temperature and Moisture of the Wheat Stored in Grain Elevators", TELSIKS 2003, Oct. 1-3, 2003, p. 823-826.*
Internet Archive Way Back Machine, "http://www.intellifarms.com/solutions/smartcables", Oct. 8, 2014, p. 1.*
Internet Archive Way Back Machine, "https://uaex.edu / publications/ pdf/mps297/s9 storage.pdf", Apr. 7, 2015, p. 1.*
International Search Report and Written Opinon of the International Searching Authority in corresponding PCT/US2013/053337 application.
OPI Systems: "Advanced Grain Management", 2011, pp. 1-65, XP002714203, Retrieved from the Internet: URL:http://www.sirajsons.pk/OPI-Integris%20Presentatlon.,pdf, pp. 25,26,31.
"Introducing OPI-Integris moisture", Jul. 1, 2011 (Jul. 1, 2011), XP055082579, Retrieved from the Internet: URL:http://www.grainsystems.ca/documents/moisture_cable.pdf, the whole document.
Erik Flojgaard Kristensen et al: "Quality Control in Grain Stores by Use of in Bedded Wireless Sensors", Int. Conf. Agricol. Eng., Jul. 12, 2012 (Jul. 12, 2012), XP-55082600, the whole document.
"Temperatur Überwachungssysteme", Nov. 12, 2001 (Nov. 12, 2001), XP055082188, Retrieved from the Internet: URL:http://supertech.dk/images/Newpdf/AGROLOGbrochureDE.pdf, the whole document.
"Temperature in grain stores and silos Duoline soft", Feb. 1, 2010 (Feb. 1, 2010), XP055082270, Retrieved from the Internet: URL:http://www.euromac.fr/wp-content/uploads/2010/02/Prospekt-DLS-soft-en-web.pdf, the whole document.
"SafeTrack Grain Temperature Monitoring System Monitor Your Grain, Anytime, Anywhere.", Apr. 30, 2012 (Apr. 30, 2012), XP055082567, Retrieved from the Internet: URL:http://safegrain.com/wp-content/uploads/2012/05/SafeTrack-Brochure.pdf, the whole document.
"Grain Watch-", Nov. 3, 2008 (Nov. 3, 2008), pp. 1-2, XP055082542, URL:http://liroselectronic.com/gw/documents/GWdatablad20081103ru.pdf, the whole document.
"Resistance to Airflow of Grains, Seeds, Other Agricultural Products, and Perforated Metal Sheets"; pp. 528-538; Mar. 1996, ASAE Standards 1998.
"Management of Stored Grain With Aeration—Airflow and Equipment"; Revised 1991.
S.J. Ray, L.O. Pordesimo, LR. Wilhelm; "Airflow Resistance of Some Pelleted Feed"; vol. 47(2): pp. 513-519; "Transactions of the ASAE"; © 2004 American Society of Agricultural Engineers ISSN 0001-2351.
S.O. Jekayinfa; "Effect of Airflow Rate, Moisture Content and Pressure Drop on the Airflow Resistance of Locust Bean Seed"; May 2006; Agricultural Engineering International; the CIGR Ejournal. Manuscript FP 06 010. vol. VIII.
"DS36C280 Slew Rate Controlled CMOS EIA-RS-485 Transceiver"; © 2004 National Semiconductor Corporation; Texas Instruments; Literature Number: SNLS097B; Jul. 2000.
BinManager LIT; GSI Total Value, Total Systems; GS-040 Oct. 2009; © 2009 by GSI Group, LLC.
"Grain Moisture Measurement with Capacitance Type Devices"; AgriChem, Inc.; Oct. 21, 1994.
R.B. McIntosh, M.E. Casada; "Fringing Field Capacitance Sensor for Measuring the Moisture Content of Agricultural Commodities"; IEEE Sensors Journal, vol. 8, No. 3, Mar. 2008.
M.E. Casada, P.R. Armstrong; "Wheat Moisture Measurement with a Fringing field Capacitive Sensor"; vol. 52(5): 1785-1791; © 2009 American Society of Agricultural and Biological Engineers ISSN 0001-2351.
M.E. Casada, P.A. Armstrong; "Wheat Moisture Measurement with a Fringing Field Capacitive Sensor"; An ASABE Meeting Presentation; Paper No. 085207; Jun. 29, 2008.
W.C. Wang, Y.Z. Dai; "A Grain Moisture Detecting System Based on Capacitive Sensor"; International Journal of Digital Content Technology and Its Applications; vol. 5, No. 3; Mar. 2011.
"PIC16F5X Data Sheet, Flash-Based, 8-Bit CMOS Microcontroller Series"; © 2004 Microchip Technology Inc.; DS41213C-p. ii-88; Sep. 27, 2004.
U.S. Appl. No. 13/180,797, filed Jul. 12, 2011, Brent J. Bloemendaal.
U.S. Appl. No. 13/569,814, filed Aug. 8, 2012, Brent J. Bloemendaal.
Paul Sumner; "Harvesting and Drying Corn"; A Guide to Corn Production in Georgia, University of Georgia, 2013, pp. 76-86 (http://www.uaex.edu/publications/PDF/MP297/9_storage.pdf).
D. Garg, D.E. Maier; "Modeling non-uniform airflow distribution in large grain silos using Fluent", pp. 754-762; $9^{th}$ International Working Conference on Stored Product Protection, Oct. 15-18, 2006, Sao Paulo, Brazil (http://spiru.cgahr.ksu.edu/proj/iwcspp/iwcspp9.html)
Dennis R. Gardisser; "9—On Farm Storage and Drying"; Grain Sorghum Production Handbook, University of Arkansas, Current, pp. 55-60 (http://search.uaex.edu/search?q=on+farm+storage+and+drying&site=default_collection&client=uaex&proxystylesheet=uaex) (unknown original publication date, but downloaded from the internet prior to Aug. 8, 2012).
"Complete Grain Management with BinManager"; IntelliAir, BinManager, (unknown original publication date, but downloaded from the internet prior to Aug. 8, 2012).
OPI Moisture Management; "Moisture Monitoring & Control"; OPI Systems; Integris USA LLC, (unknown original publication date, but downloaded from the internet prior to Aug. 8, 2012).

* cited by examiner

| Sensor Node Address | | Raw Sensor Data | | | Sensor Node Location Data | | | Caclulated | |
|---|---|---|---|---|---|---|---|---|---|
| | Sensor Node | | Reference | Moisture | | | | Moisture | Grain |
| Cable ID | Sensor Node ID | Temperature | Reference Capacitance | Moisture Capacitance | X | Y | Z | Moisture Content | Grain Depth |
| 1 | 1 | | | | | | | | |
| 1 | 2 | | | | | | | | |
| 1 | 3 | | | | | | | | |
| 1 | 4 | | | | | | | | |
| 1 | ... | | | | | | | | |
| 1 | x | | | | | | | | |
| 2 | 1 | | | | | | | | |
| 2 | 2 | | | | | | | | |
| 2 | 3 | | | | | | | | |
| 2 | 4 | | | | | | | | |
| 2 | ... | | | | | | | | |
| 2 | x | | | | | | | | |
| ... | ... | | | | | | | | |
| x | 1 | | | | | | | | |
| x | 2 | | | | | | | | |
| x | 3 | | | | | | | | |
| x | 4 | | | | | | | | |
| x | ... | | | | | | | | |
| x | x | | | | | | | | |

FIG. 12

GRAIN BIN CAPACITIVE MOISTURE SENSOR SYSTEM AND METHOD

FIELD

The present disclosure relates to grain bin moisture sensors and related methods, and more particularly, to capacitive moisture sensor cables, systems, and methods.

BACKGROUND

This section provides background information related to the present disclosure which is not necessarily prior art.

Capacitive moisture sensors have been used to detect moisture content in grain. In some cases, however, the grain needs to be positioned in the gap between the capacitive electrodes or plates. Thus, such sensors are typically used on small samples of grain that have been moved to a test set-up, and they are not readily suited for use in measuring grain inside a grain bin.

In other cases, ground electrodes are provided at opposite ends of a tubular shaped opposite polarity electrode. This means the capacitive gaps extend circumferentially around the generally tubular sensor. Thus, increasing the adjacent volume of grain for sensing requires increasing the diameter of the sensor. This can result in such a large downward force being applied on the sensors by the grain when used in large grain bins that this force cannot be supported by the grain bin roof structure.

The necessary size of moisture sensors, and associated communication links, can also be affected by the processing of raw data at the sensor node. The processing of raw data at each sensor node can result in an increased memory space and microprocessor capabilities, which generally increases the necessary size of the sensor node. As noted above, this can have a detrimental impact on the downward force exerted on the sensor nodes and ultimately on the grain bin roof structure by the grain.

SUMMARY

This section provides a general summary of the disclosure, and is not a comprehensive disclosure of its full scope or all of its features; nor are the features summarized herein essential aspects of the disclosure.

In one aspect of the disclosure a grain bin moisture sensor system is provided that includes a data collector associated with a grain bin. The data collector includes a data collector microprocessor and a data collector memory. The data collector is in communication with at least one capacitive moisture cable hanging within the grain bin. Each capacitive moisture cable includes a plurality of sensor nodes spaced at a predetermined interval along the moisture cable and each sensor node is wired in parallel to the data collector. Each sensor node includes a sensor node microprocessor and a sensor node memory coupled to a temperature sensor, a reference capacitive sensor and a capacitive moisture sensor. A main controller includes a main controller microprocessor and a main controller memory. The main controller is in communication with the data collector, wherein the main controller memory is configured in a data structure comprising grain type data, temperature data, raw reference capacitance data, raw moisture capacitance data, node identification data, physical node positional data, and a calculated moisture content for each sensor node.

In another aspect of the present disclosure a method of determining moisture contents of grain in a grain bin includes providing a plurality of sensor nodes within the grain bin. Each sensor node is provided with a sensor node memory and a sensor node microprocessor coupled to a temperature sensor, a reference capacitance sensor, and a moisture capacitive sensor. Each sensor node microprocessor stores temperature data, raw reference capacitance data, and raw moisture capacitive data in the sensor node memory. A data collector is provided that includes a data collector microprocessor and a data collector memory. A sensor node communication link is provided between the data collector and each sensor node. The data collector microprocessor receives from each sensor node and stores in the data collector memory a copy of the temperature data, the raw reference capacitance data, and the raw moisture capacitive data received from each sensor node. A main controller is provided that includes a main controller microprocessor and a main controller memory. A communication link between the main controller and the data collector is also provided. The main controller microprocessor receives from the data collector and stores in the main controller memory a copy of the temperature data, the raw reference capacitance data, and the raw moisture capacitive data, from each sensor node. The main controller processor determines a calculated moisture content based upon the raw reference capacitance data, and the raw moisture capacitive data for each sensor node stored in the main controller memory. The main controller processor stores the calculated moisture content in the main controller memory for each sensor node.

In another aspect of the present disclosure a method of determining moisture contents of grain in a grain bin includes providing a plurality of capacitive moisture sensor nodes on a plurality of moisture cables within the grain bin. Power is provided to a selected one of the plurality of moisture cables without activating the plurality of capacitive moisture sensor nodes on the selected moisture cable. A selected one of the plurality of capacitive moisture sensor nodes on the selected moisture cable is activated. Capacitive moisture data and temperature data is obtained from the activated sensor node on the selected moisture cable. The selected one of the plurality of capacitive moisture sensor nodes is returned to an inactive state. A subsequent one of the plurality of capacitive moisture sensor nodes on the selected moisture cable is activated until each of the sensor nodes on the selected cable has been individually activated. Power is terminated to the selected one of the plurality of moisture cables. Power is provided to a subsequently selected one of the plurality of moisture cables until each of the plurality of moisture cables has been individually powered.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 12 is a raw data memory data structure map of the main controller of the system of FIG. 1;

Corresponding reference numerals indicate corresponding parts throughout the several views of the drawings.

DETAILED DESCRIPTION

Figure 1:
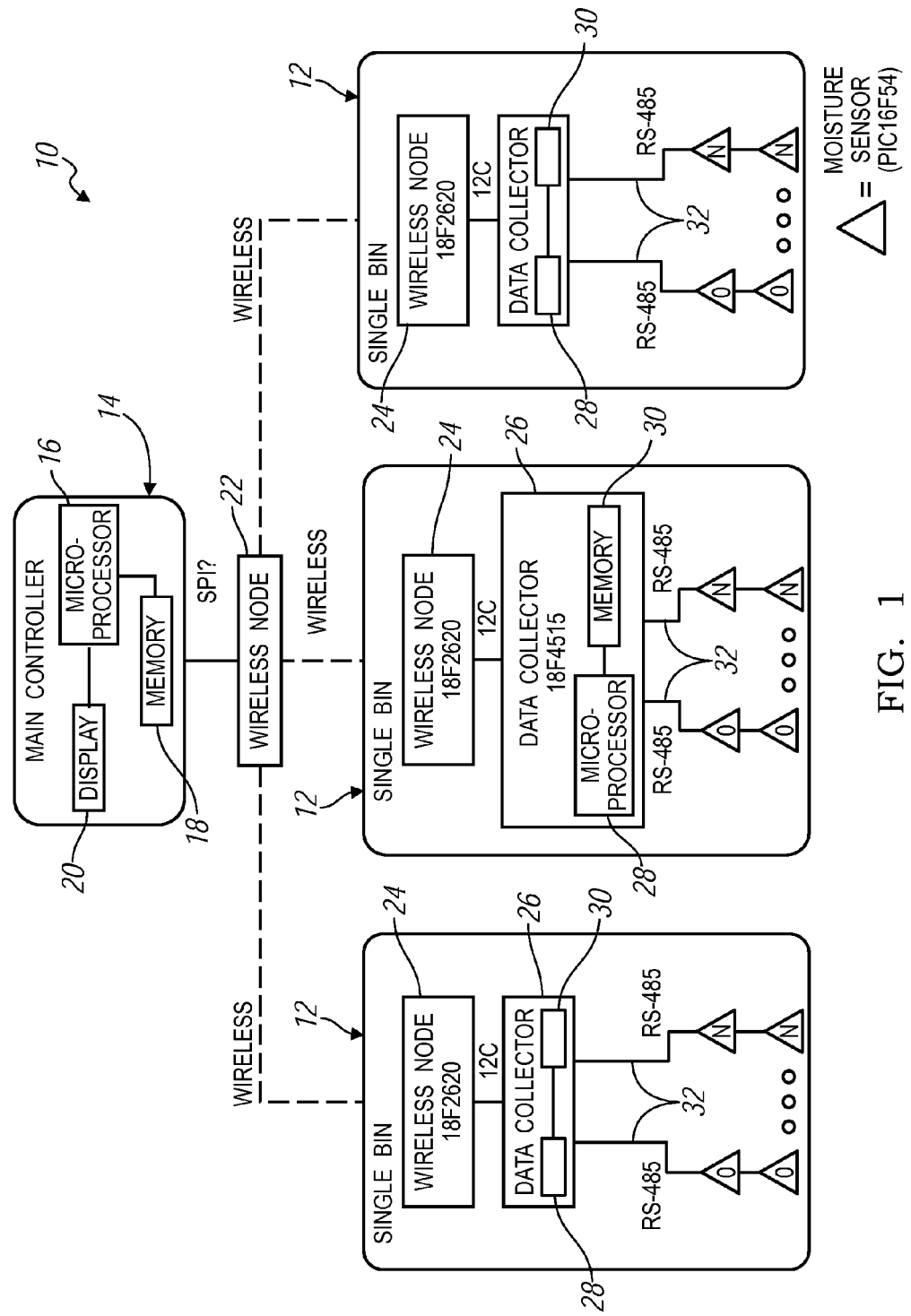
FIG. 1 is an overview of a grain bin capacitive moisture sensor system in accordance with the present disclosure.

Example embodiments will now be described more fully with reference to the accompanying drawings. Numerous specific details are set forth in the exemplary embodiments described herein, such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

FIG. 1 provides a block diagram of a system 10 for collecting moisture data from a plurality of grain bins 12. A farm or aggregator may include a plurality of grain bins 12 that are all controlled by a single main controller 14 including a microprocessor 16, memory 18, and a display 20. All of the memory described herein, including memory 18, is non-transitory computer-readable memory. Main controller 14 communicates with each grain bin 12 via wireless nodes 22, 24. For example wireless node 22 can be an 802.15 module and each wireless node 24 can include a PIC 18F2620 microprocessor.

A wireless node 24 of each grain bin provides an input and output communication link between main controller 14 and a data collector 26 including a microprocessor 28 and memory 30. For each grain bin 12, a plurality of moisture cables 32 are in communication with a data collector 26 including a microprocessor 28 and memory 30. Each moisture cable 32 includes a plurality of sensor nodes 34 positioned at intervals along the length of each cable 32. Each sensor node 34 of each cable 32 is electrically coupled in parallel to data collector 26.

Figure 2:
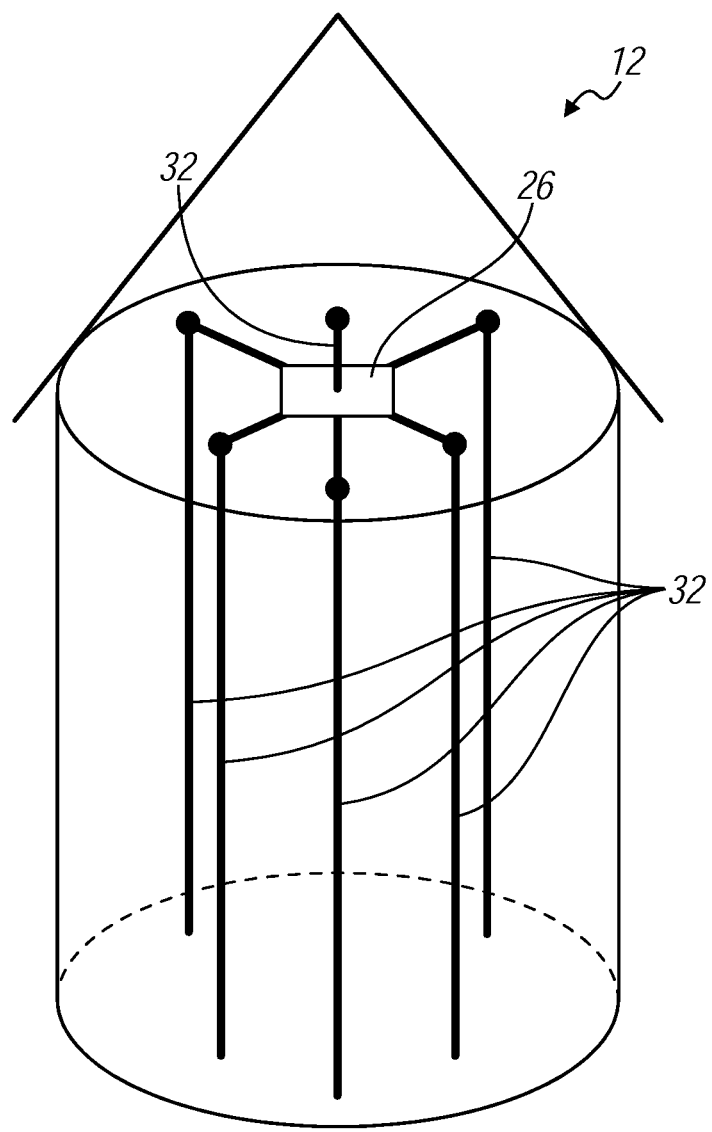
FIG. 2 is a perspective representation showing a distribution of capacitive moisture cables within a grain bin of the system of FIG. 1.
Figure 3:
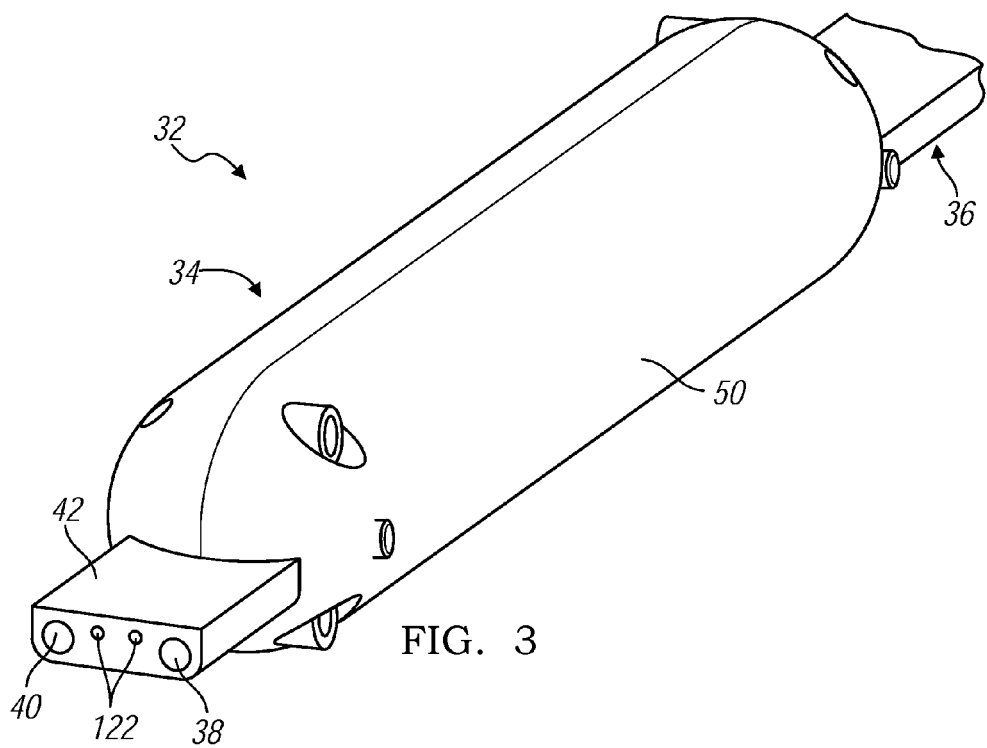
FIG. 3 is a perspective view of a capacitive moisture cable sensor node of a capacitive moisture cable of FIG. 2.
Figure 4:
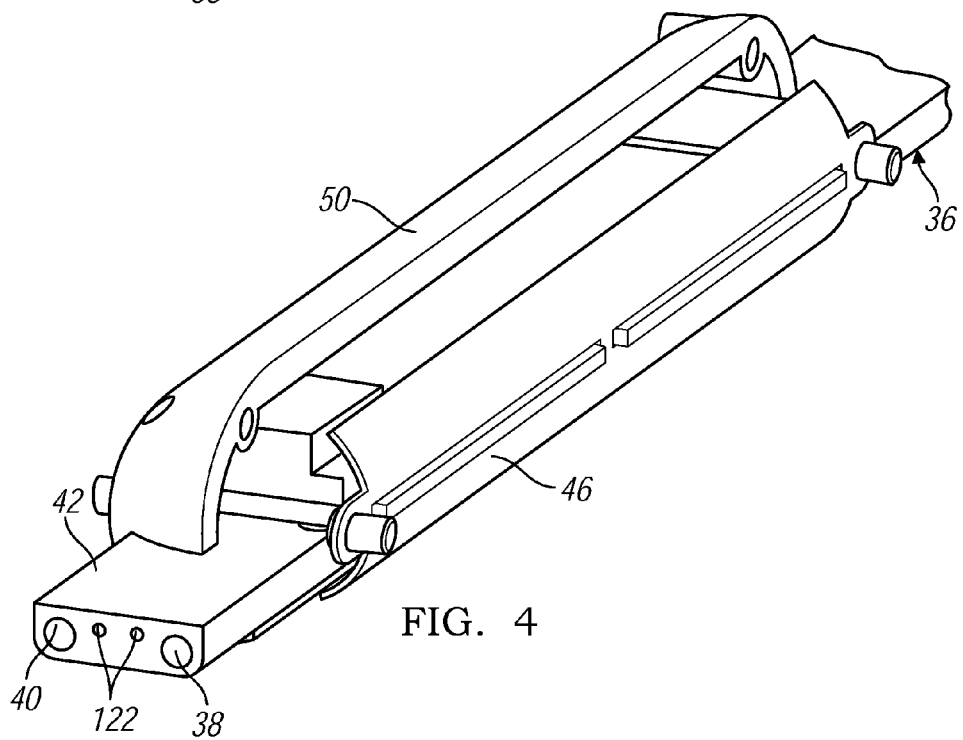
FIG. 4 is a perspective view of the capacitive moisture cable sensor node of FIG. 3 with one half of the housing removed showing the longitudinal part line thereof.
Figure 5:
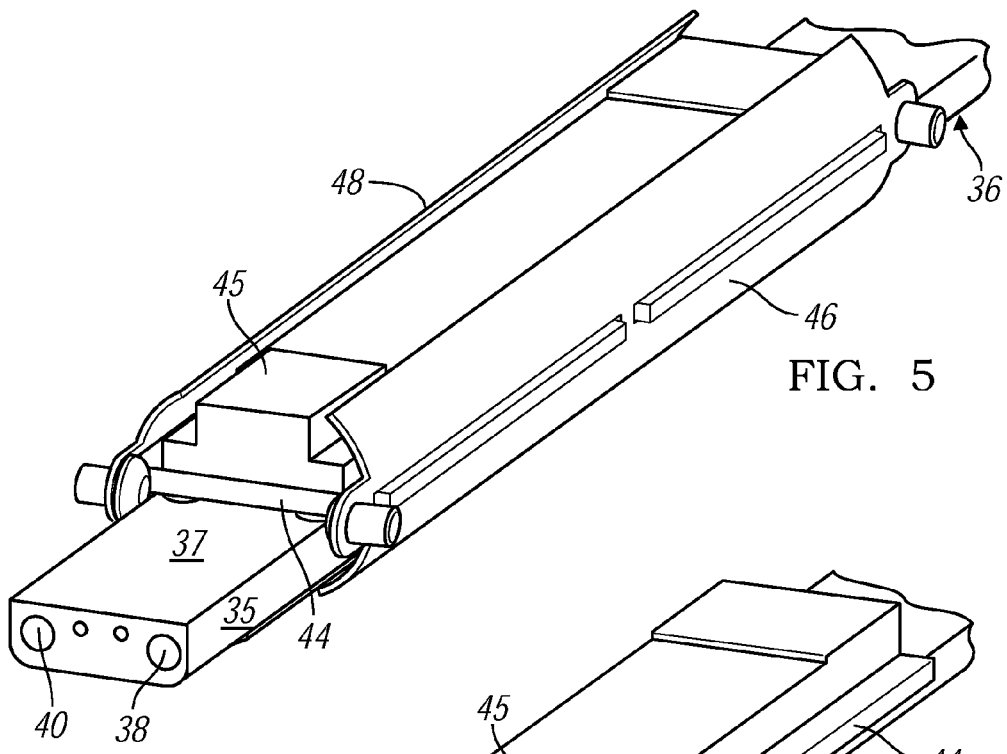
FIG. 5 is a perspective view of the capacitive moisture cable sensor node of FIG. 3 with the housing removed.
Figure 6:
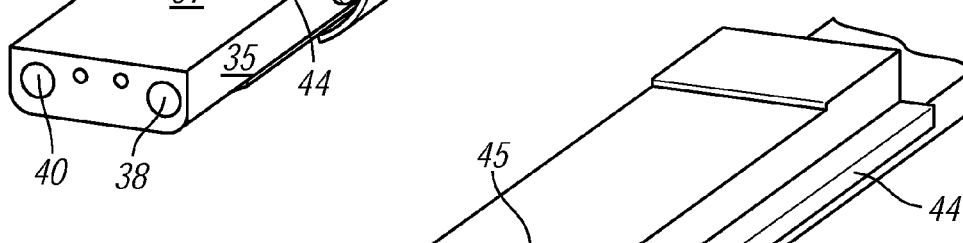
FIG. 6 is a perspective view of the capacitive moisture cable sensor node of FIG. 3 with the housing and capacitive plates removed.
Figure 7:
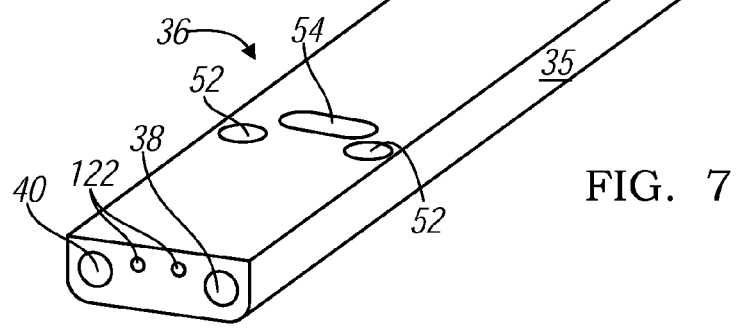
FIG. 7 is a perspective view of the wiring cable of the capacitive moisture cable sensor node of FIG. 3.

Moisture cables 32 are spaced throughout the interior of grain bin 12 as diagramed in FIG. 2. It should be appreciated that FIG. 2 is a diagrammatic representation that has been simplified to improve understanding. Each moisture cable 32 is typically physically suspended from and supported by the roof structure of the grain bin 12. Similarly, data collector 26 associated with grain bin 12 can be provided above the grain storage area, so essentially no downward force is exerted on data collector 26 by grain in grain bin 12. For example, data collector 26 can be mounted to the roof structure outside grain bin 12 or inside grain bin 12 near a top of the roof structure.

Referring to FIGS. 3-7, each moisture cable 32 includes a wiring cable 36. Wiring cable 36 includes a pair of main conductors 38 and 40. For example, main conductor 38 can provide the ground with main conductor 40 providing the opposite polarity. Main conductors 38, 40 are spaced apart from each other along a conductor plane CP passing through the conductors. Positioned in the space provided between main conductors 38, 40 are a pair of communication signal wires 122. Conductors 38, 40 and signal wires 122 are insulated from each other and the outside environment by electrically insulating material 42. The overall cross-sectional shape of wiring cable 36 is generally rectangular to allow for increased distance or spacing between main conductors 38, 40, by placing each main conductor adjacent 38, 40 one of the short sides 35 of the rectangular cross-section.

Sensor nodes 34 also include a circuit board 44 positioned against one of the long sides 37 of a rectangular cross-section of wiring cable 36. Circuit board 44 is generally planar with a rectangular shape having primary length and width dimensions in a circuit board plane BP that is parallel to conductor plane CP. Extending along opposing sides defining the length L of the circuit board 44 is a pair of opposing capacitive plates 46, 48. Opposing capacitive plates 46, 48 likewise extend along a corresponding length of the wiring cable 36; adjacent each of the short sides 35 of wiring cable's 36 rectangular cross-section. Circuit board 44 includes circuit board componentry 45 mounted thereon, such as sensor node microprocessor and memory.

Ground plane plate 46 is positioned adjacent a corresponding length of main ground conductor 38, and the opposite polarity plate 48 is positioned adjacent a corresponding length of opposite polarity main conductor 40. Opposing capacitive plates 46, 48 can be positioned generally perpendicular to the conductor plane CP and circuit board plane BP. Each capacitive plate 46, 48 can extend only outside a plane extending along the inside edge of adjacent main conductor 38 or 40 and perpendicular to the conductor plane CP and circuit board plane BP.

Power is provided to circuit board 44 via main conductors 38, 40. Communication to and from each sensor node is provided via signal wires 122. Portion of electrically insulating material 42 is removed to enable signal wires 122 and main conductors 38, 40 to be electrically coupled to circuit board 44 via spring loaded pogo pins. Electrically insulating material 42 can be removed using heat, mechanical abrasion, or another technique to provide a pair of main hollows 52 exposing main conductors 38, 40 and at least one secondary hollow 54 exposing secondary conductors 122.

Circuit board 44, capacitive plates 46, 48, and a corresponding portion of wiring cable 36 are all enclosed within a two part housing 50, that provides a sealed inner space and define each sensor node 34. The inner space can be filled with a foam or gel to protect circuit board 44 and related sensor componentry from vibrations, impact, and environmental contaminates such as moisture. The halves of housing 50 can be coupled together using threaded fasteners. Details of circuit board 44 will now be discussed.

Figure 8:
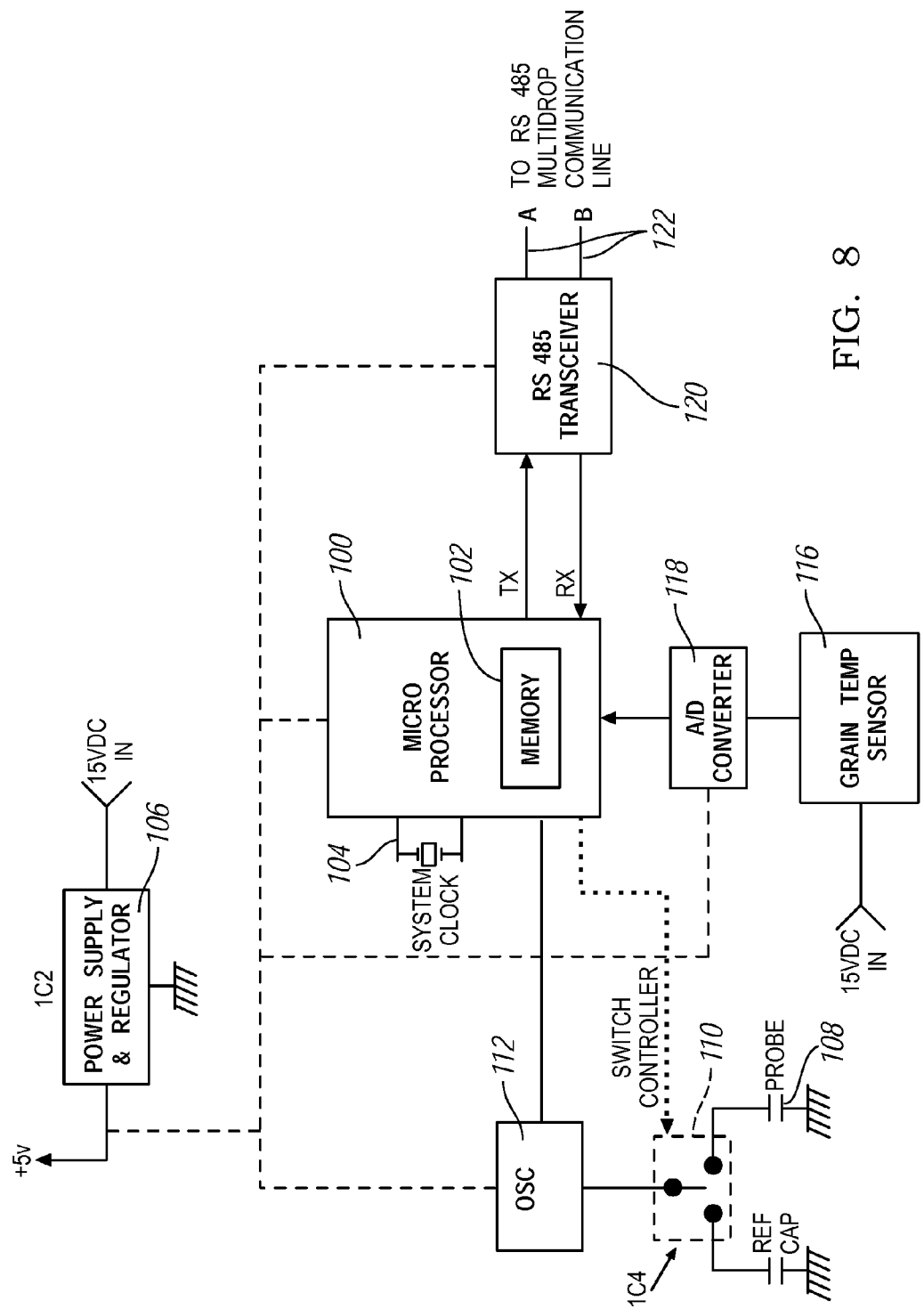
FIG. 8 is a block diagram of a circuit board of the capacitive moisture cable sensor node of FIG. 3.

Referring to FIG. 8, a block diagram of circuit board 44 for each sensor node 34 is shown. Each sensor node 34 utilizes a microprocessor 100 which may be implemented using a PIC16F54 microprocessor device. Microprocessor 100 includes internal addressable memory 102. The system clock 104 may be implemented by suitable crystal to control the clock speed of the microprocessor device. With a microprocessor device such as the PIC16F54, a suitable 4 megahertz crystal may be used. Each sensor node 34 also includes a power supply and regulator circuit 106 that supplies a nominal 5 volt DC operating voltage to the various components of the moisture sensor. The power supply and regulator circuit 106 may be implemented using an LN78L05ACZ voltage regulator circuit, which takes 15 volts DC as an input and supplies a regulated 5 volt DC output.

Microprocessor 100 collects data indicative of moisture and also data indicative of temperature. Moisture data are generated using a capacitive probe plate 108, which changes capacitance in proportion to moisture. Capacitive probe plate 108 corresponds to opposing capacitive plates 46 and 48. By measuring the change in capacitance, moisture data are derived.

More specifically, the capacitive probe plate 108 is coupled through an electrically operated switch 110 to an oscillator circuit 112. Changes in capacitance cause the oscillator circuit to change its oscillation frequency. Microprocessor 100 measures the oscillation frequency and thus collects data indicative of moisture.

To ensure that the capacitively measured moisture reading is accurate, the node moisture and temperature sensor includes a reference capacitor 114 that may be coupled to the oscillator circuit 112 (instead of capacitive probe plate 108) by operation of switch 110. As illustrated, switch 110 is controlled by microprocessor 100. Thus, microprocessor 100 controls whether oscillator circuit 112 oscillates at a frequency dictated by capacitive probe plate 108 or the reference capacitor 114.

Temperature data are obtained by a grain temperature sensor 116. Temperature sensor 116 is coupled to microprocessor 100 through an analog to digital convertor 118.

Microprocessor 100 collects moisture and temperature data from these respective sensors and communicates the collected data values through an RS-485 transceiver 120. More specifically, the data values collected by microprocessor 100 are stored in its memory 102 and then sent via the transmit (TX) line to the RS-485 transceiver 120 when requested. Requests to transmit such data are sent from the RS-485 transceiver 120 via the receive (RX) line to the microprocessor 100. The RS-485 transceiver 120 communicates over a balanced (two data lines) cable 122 comprising a data output/receive input line A and a data output/receive input line B. According to the RS-485 protocol, lines A and B are 180° out of phase with one another so that noise intercepted by both lines from the same noise source are effectively cancelled out.

Figure 9:
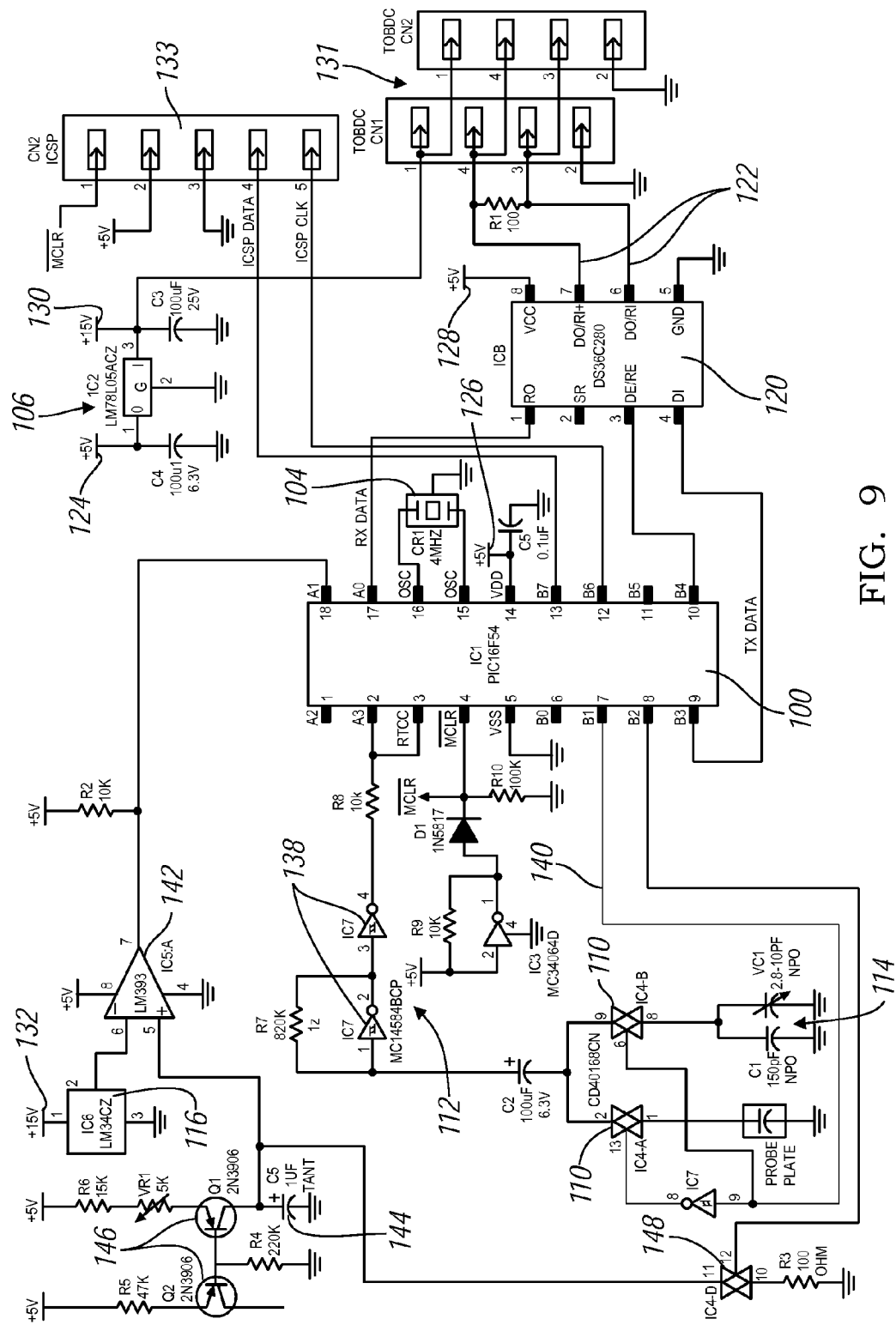
FIG. 9 is a circuit diagram of the circuit board of FIG. 7.

Referring now to FIG. 9, data lines A and B are coupled in parallel via connector or pogo pins 131 with the respective data lines of other similarly configured moisture sensors to form a distributed-sensor multidrop communication line that is deployed in the grain bin as discussed above. To allow each one of the sensors to be individually activated and polled to collect data, the microprocessor 100 of each sensor is programmed to respond to a unique identification address. When the system desires to obtain data from a particular sensor, a message is sent over balanced cable 122 and through the RS-485 transceiver 120 to the microprocessor 100, which then responds to the request for data by taking measurements from both moisture and temperature sensors and transmitting the same back through the RS-485 transceiver interface. As will be discussed below, each individual sensor is activated only when a reading from that sensor is desired. Otherwise the sensor is powered down. Connector 133 is used for programming microprocessor 100, such as to provide software updates.

One of the advantages of the cable moisture and temperature sensor system is that each sensor collects moisture and temperature data from a different location within the grain bin, and each sensor provides its raw measurement data (unique to that location within the bin) to the higher function processing systems for analysis. To gather this much data in a compact and economical package, the moisture sensor circuit shown in FIGS. 8 and 9 capitalizes on several circuit innovations to help minimize size, cost and power consumption while providing high reliability and accuracy.

Microprocessor 100 with its system clock 104 and associated RS-485 transceiver 120 are shown with connecting pin-outs as illustrated. Note that power supply and regulator circuit 106 includes a 5-volt bus 124 that supplies a regulated 5 volts to several of the circuit components, such as microprocessor 100 at its 5-volt power supply pin 126. A similar 5-volt power supply pin 128 supplies regulated 5 volts DC to the RS-485 transceiver 120. Other 5-volt supply connections are also illustrated in FIG. 8 but will not be further described here.

The power supply and regulator circuit 106 is supplied with 15 volts DC via its 15-volt bus 130. Bus 130 is on the unregulated side of the power supply which is supplied with a 15 volt DC voltage through the connector or pogo pins 131. Note that the 15 volt unregulated supply voltage is also fed to other locations within the circuit, such as to the 15-volt power supply pin 132 of temperature sensor 116.

To save power, when the particular sensor is not being polled, the 15-volt supply voltage may be switched off at the main controller. When turned off, no voltage is supplied via connector or pogo pins 131 and the entire circuit shown in FIGS. 8 and 9 is powered down. When 15 volts is applied via connector 131, the entire circuit powers up. To ensure that the microprocessor powers up in a controlled fashion, the circuit includes an undervoltage sensor 134. The undervoltage sensor responds to the 5-volt bus as sensed at 5-volt power supply pin 136 and sends a reset signal to the microprocessor 100 once the voltage levels have stabilized at the proper 5-volt value.

It will be recalled from the discussion of FIG. 8 that the oscillator 112 measures capacitance values of the probe plate 108 and also of the reference capacitor 114. These capacitors can be precision capacitors, such as NPO ceramic capacitors. In the illustrated embodiment, the oscillator circuit 112 is implemented using a pair of Schmitt trigger circuits 138, which oscillate at a nominal frequency of approximately 300 kHz; the exact oscillation frequency varies based on the capacitance value attached. In this regard, the probe plate 108 and reference capacitor 114 (in this case a pair of capacitors in parallel) are alternately switched in and out of the oscillator circuit 112 by microprocessor-controlled switch 110. Switch 110 is implemented using a pair of analog bidirectional switches that are controlled by a data value supplied on lead 140 from microprocessor 100.

When microprocessor 100 receives a command to read and furnish data, via a command from the RS-485 transceiver 120, the microprocessor reads the oscillator circuit frequency with the reference capacitor 114 switched into the circuit and then it changes the switch setting to read the oscillator frequency with the probe plate capacitor 108 switched into the oscillator circuit. Both data values are obtained and transmitted through the RS-485 transceiver 120 each time a data request is made. In this way, the moisture content is measured (based on the reading obtained using the capacitive probe plate 108). Any circuit drift or other measurement aberrations caused by temperature variation or component aging are measured and compensated for using the readings taken using the reference capacitor 114. By taking both readings both times, the moisture sensor provides highly accurate and reliable data on the sensed moisture content.

In the illustrated embodiment, the oscillator circuit 112 oscillates at a nominal frequency of around 300 kHz. While it is possible to use a microprocessor with high-speed capabilities sufficient to directly count oscillations at this cycle rate, such microprocessors can be expensive. Thus, the illustrated embodiment uses a cycle measuring technique that takes advantage of the microprocessor device's real-time clock function. To measure oscillator frequency, a register or memory location within microprocessor 100 is programmed to increment its count with each incoming pulse from the oscillator circuit, starting at a zero count and counting up until the register overflows. The microprocessor is programmed to monitor and record the number of times this register overflows within a predetermined time interval, and then also read the value extant in the register after the measurement's time interval is up. The recorded number of overflows and the extant register value at the end of the measurement cycle are then collectively used to calculate the oscillator frequency and this value is then converted to an equivalent moisture content reading by applying a capacitance-to-moisture conversion.

Temperature measurements are obtained by temperature sensor 116, which provides an analog value that is converted into a digital value by the analog-to-digital convertor 118. While there are prepackaged analog-to-digital convertor devices that may be used for this function, the illustrated embodiment saves costs by performing the analog-to-digital conversion using comparator 142, configured to compare the output from temperature sensor 116 with a ramping up sawtooth voltage on capacitor 144. Essentially, capacitor 144 is supplied by a constant current source 146 implemented by a pair of transistors, which can be precision transistors. The constant current source thus fills capacitor 144 at a controlled rate, such that the voltage on capacitor 144 ramps up linearly from zero to the power supply voltage (plus 5 volts) in sawtooth fashion. By operating electrically controlled switch 148, microprocessor 100 periodically shorts capacitor 144 to ground, thus resetting the capacitor's voltage to zero, restarting the sawtooth waveform. Once the short is lifted, the voltage on capacitor 144 ramps up at a constant rate dictated by the constant current source 146, making the voltage across capacitor 144 a reference source with which comparator 142 compares the output of the temperature sensor 116.

Figure 10:
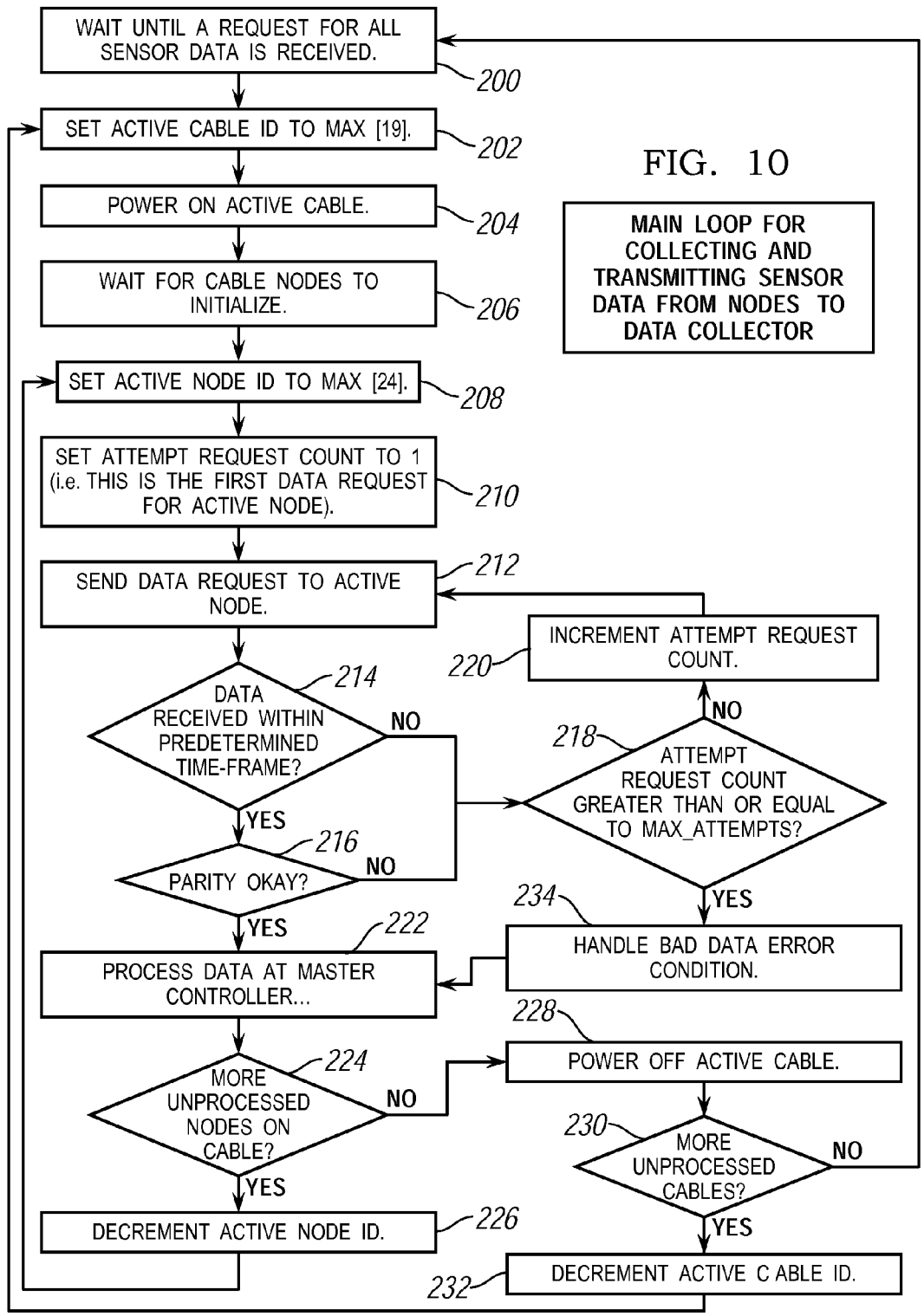
FIG. 10 is a main loop flow chart for the data collector to collect data from sensor nodes and transmit the data for the main controller of the system of FIG. 1.

Referring to FIG. 10, a main loop for collecting and transmitting data from sensor nodes 34 to data collector 26 is provided. At box 200, data collector waits until a request for sensor data from a bin is received from main controller 14. Once a request is received, then the active cable identifier is first set to a maximum value at box 202. For example, if there are 19 cables in the grain bin, then the active cable identifier is set to 19. At box 204, microprocessor 28 turns the power on to the active cable 32 corresponding to that cable identifier. Microprocessor 28 waits for sensor nodes 34 on the active cable 32 to initialize at box 206.

At box 208, the active sensor node identifier is set to a maximum value. For example, if there are 24 sensor nodes on the moisture cable 32, then the sensor node identifier is set to 24. At box 210, the attempt request count is set to 1, representing the first data request for the sensor node 34 being polled. A data request is sent to the active sensor node at box 212. If data is received by data collector 26 within a predetermined time period at box 214, then the parity of the data is checked at box 216.

If data is not received within the predetermined time period at 214, or the parity of the data is not okay, then microprocessor 28 logic continues to box 218 to determine whether the attempt request count is greater than a predetermined value corresponding to the maximum number of attempts. If not, then the attempt request count is increased by one at box 220 and the logic returns to box 212 to send another data request to sensor node being polled; that is, to the active sensor node on the active moisture cable in the grain bin being measured.

If the data is received 214 and the parity is okay at 216, then the data is sent to main controller 14 for processing at box 222 via data collector 26 and wireless nodes 11 and 24. Once microprocessor 100 determines that the attempt request number exceeds a predetermined maximum value at box 218, then a bad data error value for each of the temperature, reference capacitance, and probe moisture probe capacitance is provided for the active sensor node at box 234, which error value is sent to the main controller at 222.

Microprocessor 28 determines if there are additional sensor nodes on the active cable from which data has not been collected at box 224. If so, then the active node identifier is reduced by one at box 226 and the logic returns to box 210 to set the attempt count to 1 for the new active sensor node. If not, then the active cable is powered off at box 228.

A determination is made as to whether there are additional moisture cables in the grain bin from which data has not been collected at 230. If so, the active cable identifier value is decreased by 1 at box 232, and the cable corresponding to the decreased cable identifier is powered up while the prior active cable is powered down at box 204. If not, then the moisture cable is powered down and data collector 26 simply waits to receive another data polling request at 200.

Figure 11:
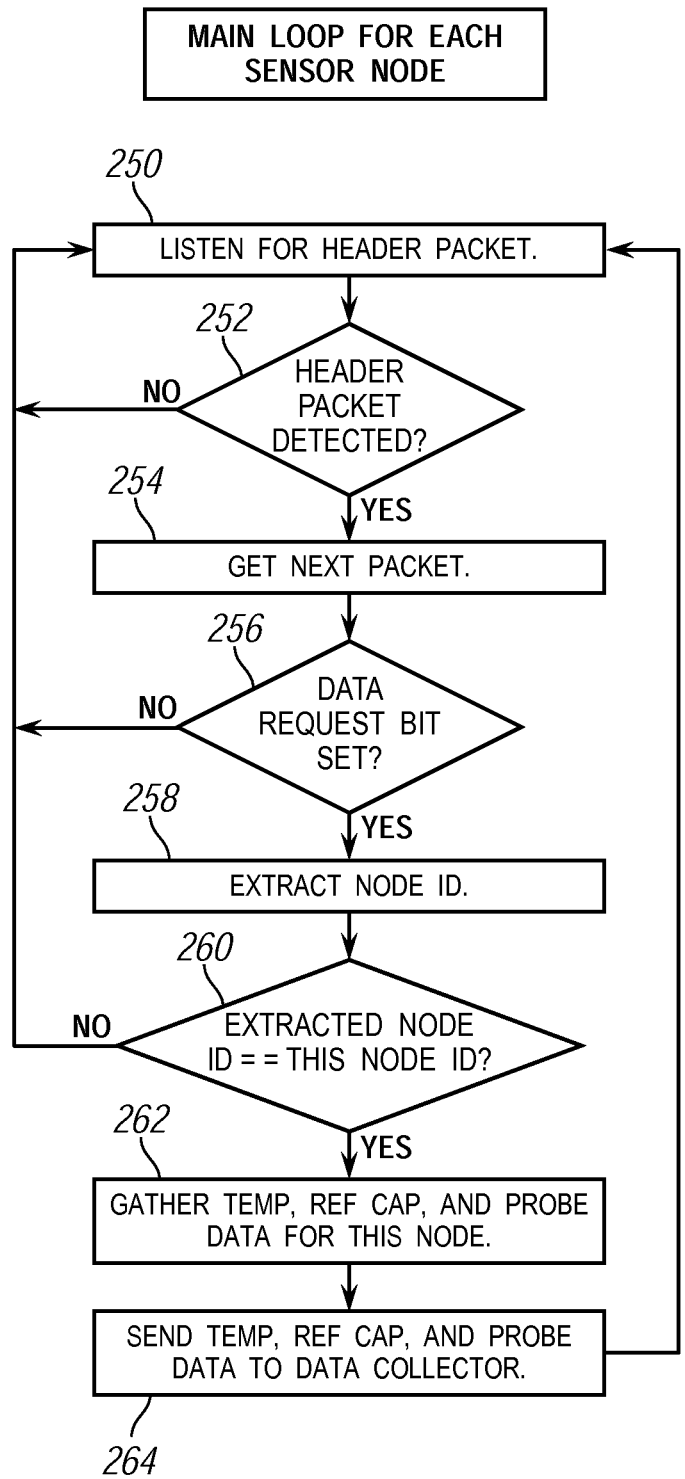
FIG. 11 is main loop flow chart for the sensor node microprocessor to collect and send data in response to a polling request from the data collector of the system of FIG. 1.

Referring to FIG. 11, a main loop is provided for each sensor node microprocessor 100. When a moisture cable 32 is powered up, microprocessor 100 is set to listen for a header packet at box 250. If it is determined that no header packet is detected at box 252, then microprocessor continues listening for a header packet at 250. If a header packet its detected at box 252, then the packet is received at 254 and a determination is made as to whether the header packet is a data request bit set at 256. If not, then microprocessor 100 returns to listening at box 250. If so, then the active node identifier is extracted from the header packet at box 258. If the extracted node identifier matches that node identifier at 260, then the temperature, reference capacitance data and moisture capacitance data is collected at and sent to data collector 26 at box 264.

As should be apparent from the above discussion of FIGS. 10 and 11, a plurality of capacitive moisture sensor nodes 34 are provided on a plurality of moisture cables 32 within grain bin 12. Power is provided to a selected one of the plurality of moisture cables 32 without activating the plurality of capacitive moisture sensor nodes 34 on the selected moisture cable 34. Powered but inactive sensor nodes 34 draw essentially no current. Particularly in view of the powering of only one moisture cable 32 at a time, the inactive sensor nodes 34 do not generate problematic heat, which could negatively impact the data being collected.

A selected one of the plurality of capacitive moisture sensor nodes 34 on the selected moisture cable 32 is activated. Capacitive moisture data and temperature data is obtained from the activated sensor node 34 on the selected moisture cable 32. The selected one of the plurality of capacitive moisture sensor nodes 34 is returned to an inactive state. A subsequent one of the plurality of capacitive moisture sensor nodes 34 on the selected moisture cable 32 is activated until each of the sensor nodes 34 on the selected cable 32 has been individually activated. Power is terminated to the selected one of the plurality of moisture cables 32. Power is provided to a subsequently selected one of the plurality of moisture cables 32 until each of the plurality of moisture cables 32 has been individually powered and each of the sensor nodes 34 has been individually activated and had data collected therefrom.

As indicated above, the data that is sent to main controller 14 from each sensor node is raw data that has not yet been processed into a moisture content value. One benefit to this is that there is no need to provide data collector 26 with sufficient memory and processing power to convert the raw data into a moisture content value. Another benefit is that data collector need not have information about the type of grain that is being stored in the grain bin, which information will typically already be stored in the main controller for other reasons.

A data structure map of a portion of memory 18 of main controller 14 is exemplified in FIG. 12. The raw data collected from all of sensor nodes 34 of a grain bin 12 can be stored in main controller memory 18 as indicated in this data structure map. The raw data includes temperature data, reference capacitance data, and moisture capacitance data. Because the unprocessed raw data from each sensor node is copied into main controller memory 18, there is no need to process any of this raw data at sensor nodes 34 or data collector 26. This the memory and processing power required to process the raw data need only exist at the main controller; and need not be duplicated at sensor nodes 34 or data collector 26.

One way to provide the system with the programming necessary to convert the raw data into a calculated moisture content at each sensor is using a curve that plots a ratio of measured capacitance to reference capacitance against actual measured moisture content. A temperature factor such as ((T−80)×0.046), where T is the measured temperature, can be applied to account for temperature differences. A formula can be derived to match the curve. This formula may be different for different grains. One exemplary formula can be:

$$\text{Moisture \%} = (A \times ((B - (C_m/C_r))^C) - ((T-80) \times 0.46)$$

Where:
A, B, and C are constants determined empirically for each grain type;
$C_r$ is the raw reference capacitance data;
$C_m$ is the raw measured capacitance data; and
T is temperature in degrees Fahrenheit.

Once formulas are derived for each grain, then they can be programmed into main controller 14 for use in converting the raw data into a calculated moisture data. Thus, calculated moisture content value is determined by main controller 14 based upon these three pieces of raw data, which can be stored in memory 18 in accordance with the data structure map exemplified in FIG. 12.

Another option is to provide a lookup tables for each grain type. For example, a look-up table correlating the $C_m/C_r$ ratio to an initial moisture content value can be programmed into main controller 14. A temperature adjustment look-up table can be provided in main controller memory 18 to adjust the initial determined moisture content value based on the temperature data.

The physical location of each sensor node within the grain bin is important. Thus, as shown in FIG. 12, a single data structure map can include both the sensor node address and the physical coordinates of the position of the various sensor nodes 34 within a grain bin 12. This locational correlation information can be entered into main controller memory 18 upon initial installation and set-up of the moisture cables within the grain bin.

One reason physical location of each sensor node is important is to enable a determination of the grain depth in bin 12 and the depth of sensor nodes 34 below the surface of the grain. If there is no grain surrounding a particular sensor node 34, then system 10 will record a no-adjacent-grain value such as zero for any data that is outside a predetermined range for moisture capacitance. For example, a ratio of measured capacitance to reference capacitance that is less than 3% for a sensor node 34 can indicate that there is no grain adjacent that sensor node 34. As a result, main controller 14 can determine the height of the grain in grain bin 12 based upon such anomalous readings. For example, with sensor nodes 34 spaced four feet apart, system 10 can assume the grain bin fill height at a moisture cable 32 is two feet below the lowest sensor node returning a no-adjacent-grain-value.

This grain fill height information can be used to determine a desired airflow rate as part of a method of controlling the operation of variable speed ventilation fans as described in commonly owned U.S. patent Ser. No. 13/180,797 filed by Bloemendaal et al. on Jul. 12, 2011 and entitled "Bin Aeration System," which is hereby incorporated by reference herein in its entirety.

Figure 13:
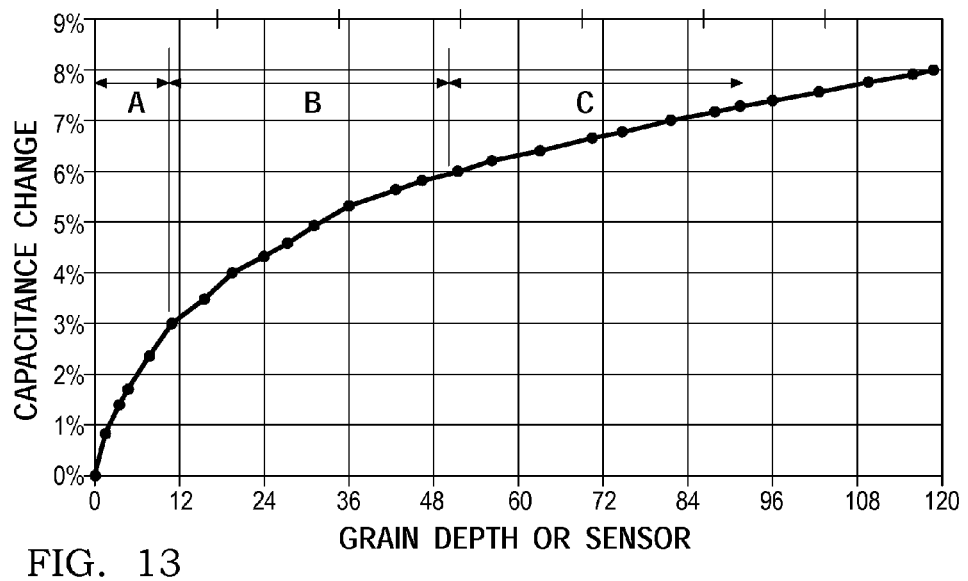
FIG. 13 is a graph of percent capacitance change to the grain depth of the sensor node.

This grain height information can also be used to apply a grain depth adjustment factor to the calculated moisture content determined for each sensor node 34. In the exemplary moisture calculation equation provided above, ((T−80)×0.46) is a temperature adjustment factor. A compaction adjustment factor can be similarly applied based on empirical data which might generate a curve similar to that shown in FIG. 13. For example, the curve of capacitance change to pressure could be divided in three regions: a first high slope region for adjusting moisture data calculated from low depth sensor nodes (region A in FIG. 13); a medium slope region for adjusting moisture data calculated from moderate depth sensor nodes (region B in FIG. 13); and a low slope region for adjusting moisture data calculated from deep sensor nodes (region C in FIG. 13). An alternative to the main controller microprocessor being programmed to use such slope formulas for compaction adjustment, is to provide a look-up table in the memory of the main controller to be used by the microprocessor to adjust the moisture content value based on grain depth calculated for each sensor node 34.

Figure 14:
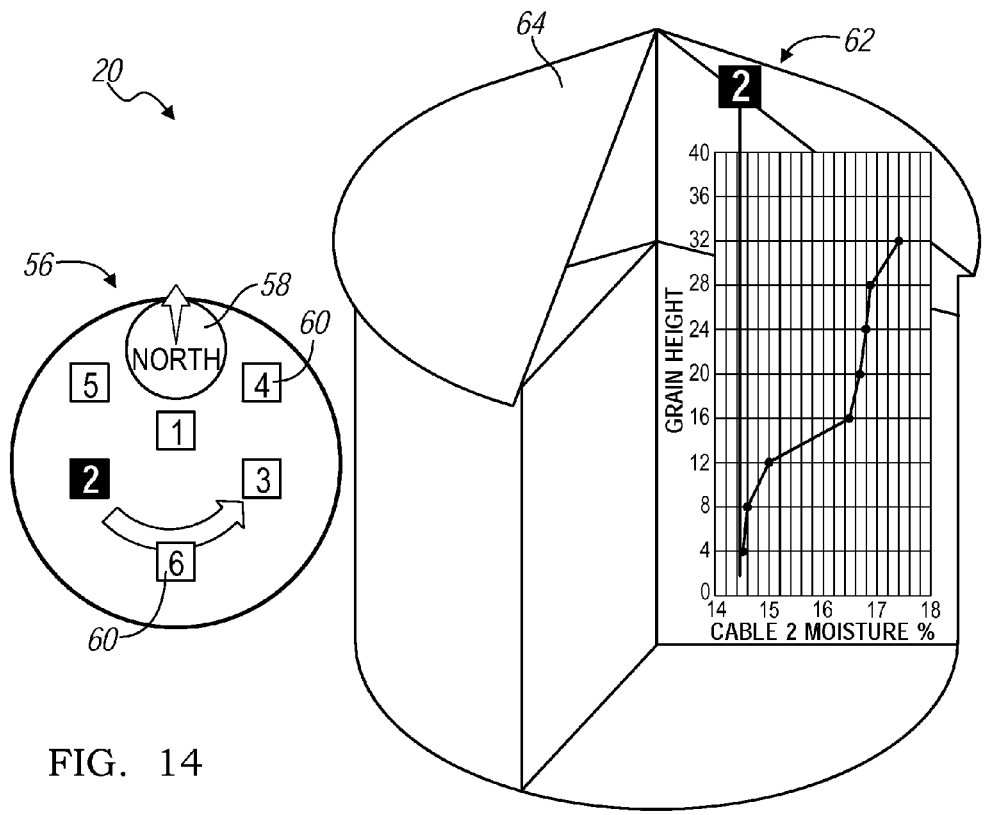
FIG. 14 is a controller display screen image representing the radial location of the moisture cables in the grain bin and displaying moisture data for a selected moisture cable.

Another reason the physical location of each sensor node is important is to enable the data to be graphically displayed so that an area or pocket of high moisture content grain can be identified by the user. FIG. 14 provides a graphical screen display that can be selectively displayed on display 20 of the main controller 14. On the left portion of display screen 20 is a diagrammatic plan view representation showing the radial or horizontal positioning of moisture cables 32 within a grain bin 12. In this embodiment, 6 moisture cables 32 are present in grain bin 12 organized in an inner 3-cable triangular configuration and an outer 3-cable triangular configuration inverted relative to the inner triangle. The plan view representation also includes a positional or orientational reference, which in this case is an indication of North.

A user can select an individual cable 32 to have the moisture data displayed for sensor nodes 34 of selected cable 32. For example, each of boxes 60 can be an on-screen button that a user presses to select the corresponding moisture cable 32. Alternatively or additionally, a user may enter the number corresponding to the desired moisture cable 32 on a keypad to select calculated moisture data display of the corresponding moisture cable 32. Upon selection, the selected cable box 60 can be highlighted in a different color.

Turning to the right side of the display screen, a graphical perspective view 62 with a removed pie-shaped portion displaying the moisture calculated data value for a selected cable 32 indicated in the left portion of display screen 20 is provided. The moisture data graphic also includes an indication of the upper surface of the grain 64, which is derived from data provided by all moisture sensor nodes 34 in the grain bin 12. The image graphically displays the moisture data in a vertical orientation that substantially corresponds to the vertical position of the sensor nodes. Thus, the grain height or grain depth can be plotted on the vertical axis, and the calculated moisture content can be plotted on the horizontal axis.

Cable selection image 56 on the left and the graphical moisture data graphic 62 on the right can simultaneously appear on the same display screen 20 as shown in FIG. 14. Alternatively, the main controller 14 can permit the user to toggle between displaying the cable selection graphic 56 and the graphical moisture data graphic 62 sequentially over the same display screen space.

The physical location of each sensor node 34 is also important in order to permit corrective action directed to the problematic area or pocket of grain. For example, the problematic grain might be selectively removed from the grain bin for drying. One exemplary system that could facilitate such selective removal of a pocket of grain from the grain bin is disclosed in commonly owned U.S. patent application Ser. No. 12/827,448, filed by Niemeyer et al. on Jun. 30, 2010 and entitled "Circular Bin Unload System and Method," which is hereby incorporated herein by reference in its entirety. For example, rather than sequentially opening all of the sumps throughout the floor to remove all of the grain bin, only the sumps that are under the problematic area or pocket of grain would be opened through which grain could be removed. Thus, the problematic grain could be selectively removed from the storage grain bin. The removed grain could be processed through a grain dryer and returned to the bin. This might be an appropriate procedure if the problematic area or pocket of grain is near the bottom of the grain bin.

As another example, if the problematic area or pocket of grain is near the top of the grain bin, only the sumps that are under the problematic area or pocket of grain would be opened. Then enough grain could be removed to create a low point in the surface of the grain above the problematic area or pocket of grain. Thus, a low resistance airflow path through the problematic area or pocket of grain can be created, and ventilation fans and heaters can be used to cause air to flow preferentially through and treat the problematic area or pocket of grain.

As another example, the grain bin could be aerated using fans and a heater, if available. As noted above, the surface of the grain in the grain bin can be manipulated to preferentially pass air through the problematic area or pocket of grain found in the grain bin. For example, grain can be selectively removed from the grain bin using the Niemeyer et al. system identified above to provide a shortened airflow path through the problematic grain pocket. Alternatively or additionally, grain can be selectively added to the bin using a variable speed grain spreader to likewise provide an airflow path through the problematic grain pocket that is shortened relative to the airflow paths that do not pass through the problematic grain pocket. Once a shortened airflow path is created to preferentially pass air through the problematic area or pocket, aeration fans can be actuated to pass air through the grain bin until the moisture level is no longer problematic.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A grain bin moisture sensor system comprising:
   a data collector associated with a grain bin and comprising a data collector microprocessor and a data collector memory, the data collector being in communication with at least one capacitive moisture cable hanging within the grain bin;
   each capacitive moisture cable comprising a plurality of sensor nodes spaced at a predetermined interval along the moisture cable and each sensor node being wired in parallel to the data collector;
   each sensor node comprising a pair of capacitive plates and a circuit board defining a circuit board plane and a sensor node microprocessor and a sensor node memory coupled to a temperature sensor, a reference capacitive sensor and a capacitive moisture sensor;
   a main controller comprising a main controller microprocessor and a main controller memory, the main controller being in communication with the data collector, wherein the main controller memory is configured in a data structure comprising grain type data, temperature data, raw reference capacitance data, raw moisture capacitance data, node identification data, physical node positional data, and a calculated moisture content for each sensor node;
   wherein the circuit board is positioned between the pair of capacitive plates with the plates positioned generally perpendicular to the circuit board plane, and wherein the plates have longitudinal sides inclining toward each other to define a corresponding pair of opposing longitudinally extending gaps.

2. The grain bin moisture sensor system of claim 1, wherein the main controller microprocessor is programmed to determine the calculated moisture content based upon a ratio of the raw reference capacitance data and the raw moisture capacitance data.

3. The grain bin moisture sensor system of claim 2, wherein the main controller microprocessor is further programmed to determine the calculated moisture content based upon the temperature data.

4. The grain bin moisture sensor system of claim 3, wherein the data structure further comprises a calculated grain depth determined for each sensor node, and wherein the main controller microprocessor is further programmed to determine the calculated moisture content based upon the calculated grain depth.

5. The grain bin moisture sensor system of claim 1, wherein the main controller further comprises a display screen selectively providing a graphical representation of the calculated moisture content for selected sensor nodes as positioned within the grain bin.

6. The grain bin moisture sensor system of claim 5, wherein the at least one moisture cable is a plurality of moisture cables, and wherein the display screen is selectively provided with a graphical representation of the plurality of moisture cables as positioned laterally within the grain bin and a positional reference indictor appears on the display screen to permit a user to select one of the plurality of moisture cables.

7. The grain bin moisture sensor system of claim 1, wherein the data structure further comprises a calculated grain depth for each sensor node.

8. The grain bin moisture sensor system of claim 7, wherein the main controller microprocessor is programmed to store a no-adjacent-grain-value for any sensor nodes having a raw moisture capacitance data to raw reference capacitance data ratio that is less than a predetermined amount.

9. The grain bin moisture sensor system of claim 8, wherein the main controller microprocessor is programmed to calculate a grain height for the grain bin at each moisture cable based upon the no-adjacent-grain-value recorded for the sensor nodes.

10. The grain bin moisture sensor system of claim 1, wherein the data collector is a plurality of data collectors, and each data collector is associated with a different grain bin, and wherein each data collector is in wireless communication with the main controller.

11. The grain bin moisture sensor system of claim 1, wherein each sensor node further comprises a wiring cable positioned between the conductive plates and including a pair of conductors defining a conductor plane that is parallel to the circuit board plane.

12. The grain bin moisture sensor system of claim 11, wherein the wiring cable includes a second pair of conductors positioned between the first pair of conductors.

13. A method of determining moisture contents of grain in a grain bin comprising:
   providing a plurality of sensor nodes within the grain bin;
   providing each sensor node with a pair of capacitive plates and a circuit board defining a circuit board plane and a sensor node memory and a sensor node microprocessor coupled to a temperature sensor, a reference capacitance sensor, and a moisture capacitive sensor;
   positioning the circuit board between the pair of capacitive plates and generally perpendicular to the circuit board plane;
   inclining longitudinal sides of the capacitive plates toward each other to define a corresponding pair of opposing longitudinally extending gaps;
   each sensor node microprocessor storing temperature data, raw reference capacitance data, and raw moisture capacitive data in the sensor node memory;
   providing a data collector comprising a data collector microprocessor and a data collector memory;
   providing a sensor node communication link between the data collector and each sensor node;
   the data collector microprocessor receiving from each sensor node and storing in the data collector memory a copy of the temperature data, the raw reference capacitance data, and the raw moisture capacitive data received from one of the sensor nodes;

providing a main controller comprising a main controller microprocessor and a main controller memory;

providing a communication link between the main controller and the data collector;

the main controller microprocessor receiving from the data collector and storing in the main controller memory a copy of the temperature data, the raw reference capacitance data, and the raw moisture capacitive data, for each sensor node;

the main controller processor determining a calculated moisture content based upon the raw reference capacitance data, and the raw moisture capacitive data for each sensor node stored in the main controller memory; and the main controller processor storing the calculated moisture content in the main controller memory for each sensor node.

14. The method of determining moisture contents of grain in a grain bin of claim 13, further comprising storing sensor node identification data in the main controller memory for each sensor node.

15. The method of determining moisture contents of grain in a grain bin of claim 14, further comprising storing physical sensor node positional data in the main controller memory for each sensor node.

16. The method of determining moisture contents of grain in a grain bin of claim 13, further comprising storing grain-type data in the main controller memory for the grain bin.

17. The method of determining moisture contents of grain in a grain bin of claim 13, further comprising the main controller microprocessor further determining the calculated moisture content based upon the temperature data for the sensor node.

18. The method of determining moisture contents of grain in a grain bin of claim 17, further comprising storing a grain depth for each sensor node in the main controller memory, and further determining the calculated moisture content based upon the grain depth.

19. The method of determining moisture contents of grain in a grain bin of claim 13, further comprising providing the main controller with a display screen and displaying a graphical representation of the calculated moisture content for selected sensor nodes as positioned within the grain bin.

20. The method of determining moisture contents of grain in a grain bin of claim 19, further comprising providing the plurality of sensor nodes on a plurality of moisture cables, and further comprising displaying a graphical representation of the plurality of moisture cables as positioned laterally within the grain bin and a positional reference indictor on the display screen to permit a user to select one of the plurality of moisture cables.

21. The method of determining moisture contents of grain in a grain bin of claim 19, further comprising indicating a grain surface indicative of a grain bin fill height in the graphical representation of the calculated moisture content for selected sensor nodes as positioned within the grain bin.

22. The method of determining moisture contents of grain in a grain bin of claim 13, wherein providing a data collector comprises providing a plurality of data collectors with each of the data collectors being associated with a different grain bin, and wherein providing a communication link between the main controller and the data collector comprises providing a communication link between the main controller and each of the data collectors.

23. The method of determining moisture contents of grain in a grain bin of claim 13, further comprising positioning a wiring cable a pair of conductors defining a conductor plane between the conductive plates of each sensor node and with the conductor plane parallel to the circuit board plane.

24. The method of determining moisture contents of grain in a grain bin of claim 23, further comprising providing the wiring cable with a second pair of conductors positioned between the first pair of conductors.

25. A method of determining moisture contents of grain in a grain bin comprising:

providing a plurality of capacitive moisture sensor nodes on a plurality of moisture cables within the grain bin;

providing power to a selected one of the plurality of moisture cables without activating the plurality of capacitive moisture sensor nodes on the selected moisture cable;

activating a selected one of the plurality of capacitive moisture sensor nodes on the selected moisture cable;

obtaining capacitive moisture data and temperature data from the activated sensor node on the selected moisture cable;

storing a no-adjacent-grain-value for the activated sensor node if the raw moisture capacitance data to raw reference capacitance data ratio is less than a predetermined amount;

returning the selected one of the plurality of capacitive moisture sensor nodes to an inactive state; and activating a subsequent one of the plurality of capacitive moisture sensor nodes on the selected moisture cable until each of the sensor nodes on the selected cable has been individually activated;

terminating power to the selected one of the plurality of moisture cables;

providing power to a subsequently selected one of the plurality of moisture cables until each of the plurality of moisture cables has been individually powered.

26. The method of determining moisture contents of grain in a grain bin of claim 25, wherein obtaining capacitive moisture data and temperature data from each activated sensor node on the selected moisture cable comprises obtaining reference capacitive data and capacitive moisture data.

27. The method of determining moisture contents of grain in a grain bin of claim 25, further comprising providing a main controller comprising a main controller microprocessor and a main controller memory in communication with each of the plurality of moisture cables.

28. The method of determining moisture contents of grain in a grain bin of claim 27, further comprising the main controller microprocessor receiving and storing in the main controller memory the temperature data, the raw reference capacitance data, and the raw moisture capacitive data, for each sensor node;

the main controller processor determining a calculated moisture content based upon the raw reference capacitance data, and the raw moisture capacitive data for each sensor node stored in the main controller memory; and the main controller processor storing the calculated moisture content in the main controller memory for each sensor node.

29. The method of determining moisture contents of grain in a grain bin of claim 28, further comprising storing sensor node identification data in the main controller memory for each sensor node.

30. The method of determining moisture contents of grain in a grain bin of claim 29, further comprising storing physical sensor node positional data in the main controller memory for each sensor node.

31. The method of determining moisture contents of grain in a grain bin of claim 30, further comprising storing a grain depth for each sensor node in the main controller memory, and further determining the calculated moisture content based upon the grain depth.

32. The method of determining moisture contents of grain in a grain bin of claim 27, further comprising providing the main controller with a display screen and displaying a graphical representation of the calculated moisture content for selected sensor nodes as positioned within the grain bin.

* * * * *

UNITED STATES PATENT AND TRADEMARK OFFICE
CERTIFICATE OF CORRECTION

PATENT NO.        : 9,551,737 B2
APPLICATION NO.   : 13/569804
DATED             : January 24, 2017
INVENTOR(S)       : Brent Bloemendaal et al.

It is certified that error appears in the above-identified patent and that said Letters Patent is hereby corrected as shown below:

In the Specification

Column 9, Detailed Description, Line 19, delete "11" and insert --22--.

Column 9, Detailed Description, Line 63, delete "34" and insert --32--.

In the Claims

Column 14, Line 14, in Claim 6, delete "indictor" and insert --indicator--.

Column 15, Line 52, in Claim 20, delete "indictor" and insert --indicator--.

Signed and Sealed this
Twenty-eighth Day of March, 2017

Michelle K. Lee
*Director of the United States Patent and Trademark Office*